United States Patent
Saint-Jalmes et al.

(10) Patent No.: US 6,833,476 B2
(45) Date of Patent: Dec. 21, 2004

(54) METHOD FOR USING A CARBAMOYL FLUORIDE AS FLUORINATING AGENT

(75) Inventors: Laurent Saint-Jalmes, Meyzieu (FR); Vincent Schanen, Lyons (FR); Gilbert Guidot, Ales (FR); Hubert Kempf, Salindres (FR)

(73) Assignee: Rhodia Chimie, Boulogne Billancourt (FR)

( * ) Notice: Subject to any disclaimer, the term of this patent is extended or adjusted under 35 U.S.C. 154(b) by 0 days.

(21) Appl. No.: 10/450,600

(22) PCT Filed: Jan. 10, 2002

(86) PCT No.: PCT/FR02/00075

§ 371 (c)(1),
(2), (4) Date: Oct. 17, 2003

(87) PCT Pub. No.: WO02/055487

PCT Pub. Date: Jul. 18, 2002

(65) Prior Publication Data

US 2004/0049069 A1 Mar. 11, 2004

(30) Foreign Application Priority Data

Jan. 10, 2001 (FR) ............................................. 01/00257
Aug. 8, 2001 (FR) ............................................. 01/10593

(51) Int. Cl.$^7$ ............................................. C07C 51/58
(52) U.S. Cl. ..................................................... 562/844
(58) Field of Search ......................................... 562/844

(56) References Cited

U.S. PATENT DOCUMENTS 5,471,002 A * 11/1995 Appel et al. ................. 564/412
6,074,985 A    6/2000 Elsheikh et al. ............. 502/439

FOREIGN PATENT DOCUMENTS

| DE | 11 38 391 | 10/1962 | |
| EP | 0 152 310 | 8/1985 | ........... C07C/85/20 |
| EP | 0639 556 | 2/1995 | ......... C07C/209/74 |
| FR | 2 647 107 | 11/1990 | ........... C07C/25/13 |

OTHER PUBLICATIONS

International Search Report

* cited by examiner

*Primary Examiner*—Paul A. Zucker

(57) ABSTRACT

The invention concerns a method for using a carbamoyl fluoride as fluorinating agent. Said method consists in treating a derivative bearing a halogen-containing carbon, with a carbamoyl fluoride at a temperature not less than 70 ° C. and in maintaining the ratio between the sum of hydrofluoric acid (HF) and carbamoyl fluoride as well as between the sum of exchangeable halogen atoms, isocyanate functions and carbamoyl fluoride [(HF+carbamoyl fluoride)/(exchangeable halogen+isocyanate+carbamoyl fluoride)] at a value not more than 1.2; then in carrying out a catalysis process with tin, antimony and/or titanium salt. The invention is applicable to synthesis of fluorinated derivatives.

21 Claims, No Drawings

METHOD FOR USING A CARBAMOYL FLUORIDE AS FLUORINATING AGENT

This application is an application under 35 U.S.C. Section 371 of International Application Number PCT/FR02/00075 filed on Jan. 10, 2002.

A subject matter of the present invention is a process for the synthesis of fluorinated compounds using, as fluorine source, the carbamoyl fluoride which is in equilibrium with the isocyanate and the hydrofluoric acid.

The present invention is targeted more particularly at the synthesis of compounds simultaneously exhibiting a perfluorinated carbon, or in any case a perhalogenated carbon, and an isocyanate functional group, in particular an isocyanate functional group deriving from an aniline functional group.

The perhalogenated carbon, generally a perfluorinated carbon, is a carbon of aliphatic nature, that is to say that it has $sp^3$ hybridization.

The term "perhalogenated carbon" should be understood as meaning a carbon of $sp^3$ nature which does not carry hydrogen and which comprises, in addition to its bond with the part of the molecule carrying the isocyanate functional group, at most 2 radicals, advantageously at most 1 radical, all the other atoms being halogens; said radicals are advantageously chosen from electron-withdrawing groups, this being the case in particular when there are 2 of them. Although not perhalogenated stricto sensu, carbons carrying two halogens and one hydrogen are capable of being treated like the perhalogenated compounds in the strict sense. However, they are more sluggish. Carbons carrying exchangeable or exchanged halogens are also denoted by the term "halophoric carbon(s)".

During recent decades, and more specifically during the last decade, compounds carrying a perhalogenated and in particular perfluorinated aliphatic atom have become increasingly important in the field of agrochemistry and of pharmaceuticals. This is because these perfluorinated products, generally comprising a perfluoromethyl or perfluoroethyl radical, have physiological properties which render the molecules of which they are composed particularly active.

Consequently, numerous proposals for processes resulting in said products have blossomed. Generally, the fluorinating agent is liquid hydrofluoric acid, while the intermediate substrate or the starting substrate are isocyanates.

Mention may thus be made, in the case of anilines carrying trifluoromethyl groups, of the Occidental Chemical Corporation patent No. EP-A-129 214 and the patent of the predecessor in law of the Applicant Company, namely the European patent filed on behalf of Rhône-Poulenc Spécialités Chimiques and granted under the number EP-B-152 310.

More recently, a European patent on behalf of Hoechst A. G. was published under the number EP-A-639 556.

These documents describe various alternative treatment forms by the hydrofluoric acid route and are often a good means of appreciating the limitations of this route.

According to this technique, the starting point is the protection of the amine functional group by an isocyanate functional group, for example by phosgenation. The carbon which will have to be in a perfluorinated form in the final stage is then chlorinated, generally by the free radical route. Finally, the chlorinated compound thus obtained is subjected to a stage of chlorine/fluorine exchange in an anhydrous hydrofluoric acid medium.

Two alternative forms have to date been explored in releasing the amine from the carbamoyl fluoride obtained after the exchange; these two alternative forms are: the release of the amine by means of heating in the presence of a large excess of hydrofluoric acid to give fluorophosgene or alternatively hydrolysis in a hydrofluoric acid medium by a relatively small amount of water.

The technique using the decomposition of carbamoyl fluorides to fluorophosgene has the undoubted disadvantage of resulting in the concomitant release of fluorophosgene, the toxicity of which is much greater than that of phosgene proper, which was used as a poison gas during the First World War.

Another disadvantage of this technique is the increased consumption of hydrofluoric acid, which is a relatively expensive reactant since it has to be used in large excess.

The other techniques described, namely techniques using the in situ hydrolysis of the carbamoyl fluoride, give yields which are far from being excellent.

These low yields put a serious strain on the cost price of the final product and thus on the profitability of the complete operation.

Furthermore, the use of very large excesses of hydrofluoric acid involves subsequent recovery for economic reasons or for environmental reasons, when the industrial plant is situated inland, which recovery can be in particular:

either a recycling, as less costly, and a subsequent dehydration, which renders the recovery extremely disadvantageous as regards the cost price of the operation;

or a neutralization, followed by a recovery in value of the salts thus obtained.

Finally, during the study which led to the present invention, it was shown that, even when the aromatic ring of the molecule is depleted in electrons, the reactivity of the carbamoyl fluorides is very high and results in multiple byproducts which are injurious to the conversion yield, that is to say to the selectivity of the conversion. One of the possible routes remaining open which allows easy access to the aniline is the return to the isocyanate. Thus, during the study which led to the present invention, it was shown that it is possible to proceed from the carbamoyl fluoride to the fluorinated isocyanate, provided that particularly strict procedures are adhered to.

This part of the study has formed the subject matter of an international patent application filed in France under the number PCT/FR00/01912 under priority of the French application filed under the number 9908647. These applications are published.

This technique, although it represented a significant advance, still involved the recycling of large amounts of hydrofluoric acid. This is why the study was continued to examine whether it was possible to use the discovery according to which the carbamoyl fluoride was not the source of a large number of byproducts when it was in the presence of a significant amount of isocyanate functional groups.

This is why one of the aims of the present invention is to provide a fluorinating process which does not require a large excess of hydrofluoric acid. Another aim of the present invention is to provide a process which makes it possible to achieve high conversion yields and high reaction yields.

Another aim of the present invention is to provide a process of the preceding type which makes it possible to avoid the release, or at least to limit the release, of fluorophosgene.

These aims, and others which will become apparent subsequently, are achieved by means of a process for the treatment of a derivative carrying a perhalogenated carbon, advantageously in the benzyl or allyl position or carried by an atom exhibiting a free doublet, advantageously a chalcogen, by means of a carbamoyl fluoride, advantageously an aromatic carbamoyl fluoride (that is to say, the nitrogen atom of which is connected to an aromatic ring), characterized in that said derivative carrying a perhalogenated carbon and said carbamoyl fluoride are subjected to a temperature at least equal to 70° C., advantageously at least equal to 90° C., and in that, at said temperature of at least 70° C., the ratio Q of; on the one hand, the sum of the hydrofluoric acid (HF) and of the carbamoyl fluorides to, on the other hand, the sum of the exchangeable halogens, of the isocyanate functional groups and of the carbamoyl fluorides is maintained, throughout the duration of the reaction, at a value at most equal to 1.2, advantageously to 1; indeed even 0.9 in the final third of the final exchange.

The above ratio Q can be expressed as written below:

$$\frac{HF + \text{carbamoyl fluoride(s)}}{\text{exchangeable halogens} + \text{isocyanate} + \text{carbamoyl fluorides}}$$

This ratio is targeted at all the entities present in the reactor, whether they are in the gas phase or whether they are in (the) liquid phase(s). If, in the case where the operation is being carried out in an open (unclosed) reactor, the amount of HF in the gas phase cannot be easily determined, only the HF in the liquid phase or phases will be taken into account.

All the halogens heavier than fluorine carried by the halophoric carbon or carbons are regarded as exchangeable [exchangeable halogens are those which can be exchanged by the action of liquid hydrofluoric acid in large excess (more than 4 times stoichiometry) under autogenous pressure at a temperature of 100° C. for 10 hours].

The values indicated above are values which are expressed as equivalents or, when the functional groups are monofunctional, as moles (of substrate molecule).

The minimum overall value for the complete reaction, and thus the optimum value from the economic viewpoint, is when the ratio Q approaches the ratio:

$$\frac{\text{exchangeable halogens}}{\text{exchangeable halogens} + \text{isocyanate}}$$

This minimum value has to be observed when all the reactants are introduced at the beginning of the reaction.

However, according to the present invention, it is possible and even desirable to gradually introduce the reactants, in particular the hydrofluoric acid, to move at the beginning of the reaction from time to time to much lower values.

The invention is targeted in particular at light substrates with a carbon number of at most 50, advantageously of at most 30, preferably of at most 20 carbon atoms.

Thus, according to the present invention, it has been shown that it is possible to use the fluoride of carbamoyl fluoride(s) as fluorine source making it possible to exchange a chlorine with a fluorine.

It has thus been possible to demonstrate that this technique, provided that certain constraints are observed, makes it possible to avoid the formation of an excessively large amount of byproducts.

Under the conditions under which the invention is carried out, there is an equilibrium between the isocyanate, the carbamoyl fluoride and the dissolved HF (but the latter is in equilibrium with the gaseous form). This is the reason why it is difficult to distinguish the portion of hydrofluoric acid in the reaction mixture. This is the reason why the ratio is indicated in the form of a sum ratio.

The reaction is advantageously carried out in the presence of solvent but this is not necessary and, in particular, it is possible to use an excess of isocyanate(s) as a solvent. This is particularly true when the isocyanate is too depleted in electrons to give rise to Friedel-Crafts reactions.

It is thus preferable for the aromatic entities to exhibit, in the medium, only rings depleted in electrons. The more depleted the rings, the less likely they are to give rise to side reactions. By way of indication, it is thus desirable, for any benzene ring present, for the sum of the $\sigma_p$ Hammett constants to be at least equal to 0.2; advantageously to 0.4; preferably to 0.7.

According to the present invention, not all the exchange necessarily takes place at high temperatures (at least equal to 70° C.); only the part of the reaction where the ratio Q' is less than 0.8, preferably than 1, should advantageously take place at these high temperatures.

Q' is the ratio:

$$\frac{HF + \text{carbamoyl fluoride(s)}}{\text{isocyanate} + \text{carbamoyl fluoride(s)}}$$

Although it is possible to operate at relatively high temperatures, it is preferable for the reaction to take place at temperatures at most equal to 170° C., advantageously to 150° C., in particular in order for the solubility of the hydrofluoric acid in the medium not to be excessively low. This absence of solubility would result in excessively slow kinetics.

In order to prevent the boiling of the solvent from entraining gaseous hydrofluoric acid, it is preferable to choose solvents with a relatively high boiling point in order for this boiling point, under the operating conditions, to be greater than the working temperature. It is appropriate to choose solvents with a boiling point (starting boiling point in the case of a mixture) at atmospheric pressure of at least 100° C., advantageously of at least 120° C.

It is also advisable to choose the solvents so that they can be easily separated from the substrate and from the final product delivered.

The solvents which give good results are often those which are at least partially miscible with hydrofluoric acid and in particular from halogenated aromatic derivatives which do not react with the carbamoyl fluoride. When the solvents are aromatic solvents, it is desirable for their ring(s) to be deactivated in order to avoid side reactions between the starting substrate and the solvent, this being the case in particular when, according to one of the embodiments of the invention, a catalyst based on Lewis acid is used. The active constituent of the catalyst is chosen from Lewis acids and mixtures of Lewis acids. Generally, only a single Lewis acid is used.

The present invention is advantageous in particular when the carbamoyl fluoride used as fluorinating agent is formed from the starting substrate, which then comprises both an isocyanate functional group and a functional group carrying halogen atoms to be exchanged with fluorine. Under these conditions, it is more practical to form the carbamoyl fluoride or fluorides which will be used in the halogenation, more specifically in the fluorination by exchange of halogen in situ; that is to say that the introduction is carried out into the medium comprising the isocyanates, initial, formed as reaction intermediate or formed as final product obtained by addition of gaseous hydrofluoric acid.

This is particularly advantageous in the case where the isocyanates are aromatic isocyanates, that is to say isocyanates connected directly to an aromatic ring.

In order for the reaction to be easy to implement, it is preferable for there to be activation of the carbon carrying the heavier halogens than fluorine to be exchanged with the latter. This activation is generally due to conjugation with a pair of electrons can thus be due:

either to an unsaturation, or to the presence of an atom carrying a doublet, itself optionally bonded to an unsaturation.

This can be expressed by indicating that the substrate comprises a halophoric carbon of $sp^3$ hybridization carrying at least two halogens, at least one of which is a halogen with an atomic number greater than that of fluorine, which halophoric carbon is connected to at least one atom of low hybridization carrying an unsaturation or connected to an atom carrying a doublet capable of activating said halophoric carbon under the operating conditions of the process.

Said atoms carrying doublets are advantageously chalcogens. The effect of the chalcogen increases in proportion as its rank increases; thus, sulfur is a more effective chalcogen than oxygen from the viewpoint of the activation of the halophoric carbon.

The halophoric carbon advantageously corresponds to the formula —$CX_1X_2$—EWG, where $X_1$ and $X_2$ represent alike or different halogens and the EWG radical represents a halogen or group which represents a hydrocarbonaceous group, advantageously an electron-withdrawing group $X_3$ ($\sigma_p$ Hammett constant greater than 0); with the condition that at least one, advantageously two, of the $X_1$, $X_2$ and EWG groups are halogens other than fluorine; the hyphen indicating the free bond connecting the halophoric carbon to the $X_1$, $X_2$ and $X_3$ radical activating it being defined subsequently. Apart from the case where said atom of low hybridization carrying an unsaturation participates in a carbon-carbon bond (acetylenic bond, preferably ethylenic bond, which ethylenic bond itself advantageously participates in a ring with an aromatic nature), it may be indicated, by way of teaching, by the example that, advantageously, said atom of low hybridization carrying an unsaturation is an atom which participates in one of the following double bonds [where *C is the halophoric carbon]:

| Atom of low hybridization and unsaturation which it carries | Degree of aptitude for the exchange the reaction (easy = 1; less easy = 2 but more selective; relatively difficult = 3) | Comments |
| --- | --- | --- |
| —*C—CR"=NR' | 2 | With HF already constitutes a base HF medium [the sequence can even be found in substituted pyridines]* |
| —*C—CR"=S' | 1 | |
| —*C—C=N—NH—R' | 2 | With HF already constitutes a base HF medium* |
| —*C—CR"=N—O—R' | 2 | With HF already constitutes a base HF medium* |
| —*C—CR"=PR' | 2 | With HF already constitutes a base HF medium* |

-continued

| Atom of low hybridization and unsaturation which it carries | Degree of aptitude for the exchange the reaction (easy = 1; less easy = 2 but more selective; relatively difficult = 3) | Comments |
| --- | --- | --- |
| —*C—N=NR' | 2 | Compounds sometimes unstable, which restricts the range of the acceptable operating conditions |
| —*C—CF=CF$_2$ | 2 | |
| —*C—N=O | 2 | May give rise to very complex mixtures |
| —*C—NO$_2$ | 3 | To be avoided, may give rise to very complex mixtures |

The reaction proceeds better in proportion as the halophoric carbon atom increases in activity. The best activations are due either to the presence of a double bond between the carbon and the sulfur, as is indicated in the preceding table, or, preferably, by the presence of a chalcogen and/or of a phenyl ring, as is indicated later in the description.

To avoid side reactions, it is preferable to limit the potential amount of carbamoyl fluoride present in the reaction medium. This constraint is expressed by the fact that the molar ratio of the hydrofluoric acid and the carbamoyl fluoride, on the one hand, to the isocyanate and the carbamoyl fluoride, on the other hand, [(HF+carbamoyl fluoride)/(isocyanate+carbamoyl fluoride)] is at most equal to 1.5; advantageously to 1.2; preferably to 1; more preferably to 0.8; but it is preferable to carry out the addition of the hydrofluoric acid or of the carbamoyl fluoride gradually to a heel of solvent and of said derivative brought to the chosen reaction temperature, the presence of solvent moreover being optional.

Under these conditions, it is possible to carry out the reaction with more stringent constraints, namely that the addition is carried out at a rate such that, in the final 90% of the reaction duration situated below 100° C., advantageously below 90° C., the ratio of the hydrofluoric acid and the carbamoyl fluoride, on the one hand, to the isocyanate and the carbamoyl fluoride, on the other hand, [(HF+carbamoyl fluoride)/(isocyanate+carbamoyl fluoride)] is always at most equal to 0.5; advantageously to 0.3; preferably to 0.1.

The reaction becomes correspondingly easier as the proportion of fluorine among the halogens carried by the aliphatic halophoric carbon, that is to say of $sp^3$ hybridization, decreases and it becomes correspondingly easier as the proportion of isocyanate in the reaction mixture increases.

The reaction which is a subject matter of this communication can be used either to carry out selective exchange, leaving the final halogen heavier than fluorine on the halophoric carbon, or in particular to carry out complete exchange, the excess hydrofluoric acid being limited.

Thus, according to an advantageous form of the present invention, in particular when there are several exchanges to be carried out, the reaction can be carried out in several stages or in several steps. In a first stage, the first exchange or exchanges. (one or two exchanges) are carried out under cold conditions, that is to say at a temperature below 60° C., advantageously below 50° C., preferably below 40° C., more preferably below 30° C., and, in a second stage, the complete exchange is obtained by heating at a temperature at least equal to 70° C., advantageously to 90° C. The reaction can be easily carried out continuously in a cascade of reactors, the temperatures of which correspond to the above conditions, cocurrentwise or countercurrentwise. The use of a plug flow reactor can be envisaged.

It is in particular in this second step that the presence of a catalyst of Lewis acid type can be of use. The catalyst can be present in a (catalyst/substrate) molar ratio of 1% to 20%. If the catalyst is present throughout the exchange, it is preferable to limit its presence to a molar ratio value at most equal to 0.1; indeed even at most to 5%; advantageously from 0.5 to 5%; preferably from 1 to 3%. If the use of the catalyst is restricted to the part of the process greater than 70° C., or to the final heavy halogen of the halophoric carbon, which can be denoted by "final exchange", it is possible to be placed in the top part of the range, that is to say at a presence in a molar ration of 1 to 20%.

If the catalyst or catalysts are introduced into the mixture in the form of heavy halides, for the calculation of the ratio specified above, it will be considered, before the calculation, that all the heavy halides of the catalyst have been displaced by the fluoride of the hydrofluoric acid, the part of the hydrofluoric acid which has been used to displace said heavy halides from the catalyst no longer being available for the exchange. It is the same for the salts for which the acid associated with the anion is volatile under the operating conditions.

The most useful catalysts are antimony(V), tin(IV), tantalum and titanium(IV) salts. Antimony and in particular tin are preferred. Titanium also makes possible excellent results. These salts can be used alone or as mixtures. Generally, as the most practical, the salts of a single element are used as catalyst.

As was said above, but expressed in a different manner, the reaction becomes increasingly advantageous as the substrate and the carbamoyl fluoride belong to the same line of reaction intermediates. This can be expressed by indicating that said carbamoyl fluoride comprises an aliphatic carbon, that is to say of $sp^3$ hybridization, carrying at least two halogens, advantageously at least one, preferably two, of which are fluorine. As was said above, said aliphatic carbon carrying one or more fluorines is advantageously a benzyl carbon, that is to say that it is attached directly to an aromatic ring, this said aromatic ring advantageously being that which carries the nitrogen of the carbamoyl functional group; in other words, when a compound comprises two aromatic rings, it is preferable for the halophoric carbon atom to be carried by the same aromatic ring as that which carries the nitrogen of the carbamoyl functional group or of the isocyanate functional group.

That which has just been said above can be expressed by indicating that the carbamoyl fluoride carrying the halogen atoms to be exchanged advantageously corresponds to the following formula:

$$(R)_m\text{—Ar}(\text{—Z—}(CX_2)_p\text{—EWG})\text{—NH—CO—F}$$

where:
Ar is an aromatic ring, advantageously with six ring members, preferably a homocyclic ring;
the X groups, which are alike or different, represent a fluorine or a radical of formula $C_nF_{2n+1}$ with n an integer at most equal to 5, preferably to 2;

p represents an integer at most equal to 2;

EWG represents a hydrocarbonaceous group or an electron-withdrawing group, the possible functional groups of which are inert under the conditions of the reaction, advantageously fluorine or a perfluorinated residue of formula $C_nF_{2n+1}$ with an integer at most equal to 8, advantageously to 5; the total number of carbons of $—(CX_2)_p—$EWG is advantageously between 1 and 15, preferably between 1 and 10;

m is 0 or an integer chosen within the closed range (that is to say, comprising the limits) from 1 to 4; advantageously, m is at most equal to 2;

R is a substituent which is inert under the operating conditions advantageously chosen from halogens, advantageously light halogens (that is to say, chlorine and fluorine), and hydrocarbonaceous radicals, preferably alkyl, aryl, alkylchalcogenyl (such as alkyloxyl) and arylchalcogenyl (such as aryloxyl) radicals;

Z represents a single bond or a chalcogen atom, advantageously a light chalcogen atom (sulfur and oxygen).

Ar is advantageously monocyclic, preferably with six ring members.

The substrate corresponds more preferably to the formula below:

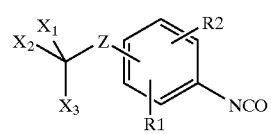

where:

Z represents a single bond or a chalcogen atom;

$X_1$ and $X_2$ represent alike or different halogens, with the condition that at least one, advantageously both, halogens are other than fluorine;

$R_1$ and $R_2$ are substituents from halogens, alkyls, aryls or nitrites;

the $X_3$ radical is a halogen or electron-withdrawing group ($\sigma_p$ constant greater than 0) which does not interfere with the reaction and in particular can be a perfluorinated group, generally denoted in the area of technology by "$R_f$";

with the condition that at least one, advantageously two, of the $X_1$, $X_2$ and $X_3$ groups are halogens other than fluorine.

When the choice is made to use solvents, mention may be made, among solvents which give satisfactory results, of chlorobenzenes, in particular monochloro-, dichloro- or trichlorobenzene, and their mixtures.

The reaction is advantageously only halted when there remains at most only one halogen atom to be exchanged out of 100 initially present, preferably when there remains no more than 1% of molecules carrying at least one halogen atom to be exchanged.

The following nonlimiting examples illustrate the invention.

Principles of the Reaction Tested

Development of a process which makes possible the preparation of para-(trifluoromethyl)benzene isocyanate (pTFMI) from para-(trichloromethyl)benzene isocyanate (pTCMI) by reaction of hydrofluoric acid according to the following diagram:

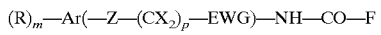

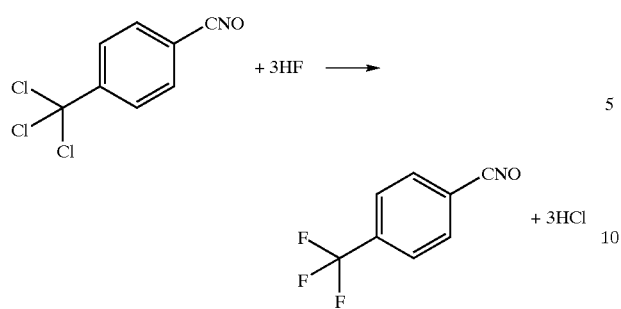

Although it does not appear here, the first reaction is the addition of the hydrofluoric acid to the isocyanate to form the carbamoyl fluoride.

EXAMPLE 1

Charge
 chlorobenzene: 90.2 g
 HF=31.5 g (3.86/pTCMI)
 pTCMI: 97.2 g (0.407 mol)

The chlorobenzene is charged and then the autoclave is closed and cooled to 0° C. The HF is introduced at 0° C. with stirring. The autoclave is equipped with a weir which makes it possible to adjust the pressure. The pressure is adjusted to ⅔ bar, the reaction medium is heated to 10° C., the pTCMI is then introduced over approximately 10 minutes and the reaction medium is then heated at 25° C. under 2.5 bar for 7 h. The reactor is degassed at 25° C. (weir opening) and is then cooled to 0° C. and left overnight.

The reaction medium is heated at 120° C. under autogenous pressure for 6 h (pressure at the end of the test 9.4 bar). The analyses are carried out by gas chromatography (GC).

Results: at the end of the fluorination at 25° C.
 carbamoyl fluoride/isocyanate proportion=24/1
 Distribution of the compounds as % area of the peaks of the chromatogram:
 $CF_3$ compounds: 11%
 $CF_2Cl$ compounds: 71.5%
 $CFCl_2$ compounds: 9.8%
 $CCl_3$ compounds: 2%

Results: at the end of the treatment at 120° C.
 carbamoyl fluoride/isocyanate proportion=77/21
 Distribution of the compounds as % area of the peaks of the chromatogram:
 $CF_3$ compounds: 79%
 $CF_2Cl$ compounds: 20%
 $CFCl_2$ compounds: 0.5%
 $CCl_3$ compounds: 0%
Estimation of the yield: sum of the organic compounds quantitatively determined: 67%

EXAMPLE 2

Charge
 chlorobenzene: 90.2 g
 HF=32 g (3.88/pTCMI)
 pTCMI: 98.4 g (0.412 mol)
 $SbCl_5$: 9.38 g (9.9 mol %)

The chlorobenzene and the $SbCl_5$ are charged and then the autoclave is closed and cooled to 0° C. The HF is introduced at 0° C. with stirring. The autoclave is equipped with a weir which makes it possible to adjust the pressure. The pressure is adjusted to ⅔ bar, the pTCMI is then introduced over approximately 10 minutes and the reaction medium is then heated at 25° C. for 7 h. The reactor is degassed at 25° C. (weir opening) and then cooled to 0° C. and left overnight.

The reaction medium is heated at 120° C. under autogenous pressure for 6 h.

Results: at the end of the fluorination at 25° C.
 carbamoyl fluoride/isocyanate proportion=16
 Distribution of the compounds as % area of the peaks of the chromatogram:
 $CF_3$ compounds: 19.5%
 $CF_2Cl$ compounds: 68.1%
 $CFCl_2$ compounds: 8.5%
 $CCl_3$ compounds: 2.7%

Results: at the end of the treatment at 120° C.
 carbamoyl fluoride/isocyanate proportion=1.5
 Distribution of the compounds as % area of the peaks of the chromatogram:
 $CF_3$ compounds: 84.3%
 $CF_2Cl$ compounds: 14.4%
 $CFCl_2$ compounds: 0.4%
 $CCl_3$ compounds: 0%
Estimation of the yield: sum of the organic compounds quantitatively determined: 86%

EXAMPLE 3

Charge
 chlorobenzene: 90.3 g
 HF=34.8 g (4.36/pTCMI)
 pTCMI: 95.3 g (0.399 mol)
 $SbCl_5$: 8.97 g (9.4 mol %)

The chlorobenzene and the $SbCl_5$ are charged and then the autoclave is closed and cooled to 0° C. The HF is introduced at 0° C. with stirring. The autoclave is equipped with a weir which makes it possible to adjust the pressure. The pressure is adjusted to 22 bar, the pTCMI is then introduced over approximately 10 minutes and the reaction medium is then heated at 120° C. for 5 h.

Results: at the end of the fluorination treatment at 120° C.
 carbamoyl fluoride/isocyanate proportion=4.2
 Distribution of the compounds as % area of the peaks of the chromatogram:
 $CF_3$ compounds: 90.5%
 $CF_2Cl$ compounds: 0.6%
 $CFCl_2$ compounds: 0%
 $CCl_3$ compounds: 0%
Estimation of the yield: sum of the organic compounds quantitatively determined: 85%

EXAMPLES 4 TO 10

Role of the Catalyst
 They are carried out according to the same procedure:
 solvent/pTCMI/catalyst are introduced into the autoclave:
 the mixture is heated at T1
 HF is introduced over X hours (per ⅔ g) and the pressure is adjusted to 2 bar (final 2 h at T=T1)
 the mixture is brought to atmospheric pressure
 the mixture is heated at T2
 final 2 h at T=T2
 the reaction mass is cooled and the residual HF is removed by sparging with nitrogen the reaction mass is diluted with methylene chloride and then quickly washed with water the analysis is carried out on the solution in methylene chloride.

the mixture is heated at T2 final X hours at T=T2 the reaction mass is cooled and the residual HF is removed by sparging with nitrogen

| | | | Operating conditions | | | | | |
|---|---|---|---|---|---|---|---|---|
| | pTCMI (g) | HF equiv. | Solvent | Mass solv. | SbCl$_5$ equiv. | T1 °C. | T2 °C. | X in hours |
| 4 | 95.3 | 3.25 | TCB | 260.8 | 10% | 60 | 120 | 2 |
| 5 | 95.86 | 3.2 | TCB | 102.6 | 10% | 30 | 120 | 2 |
| 6 | 95.8 | 3.17 | TCB | 102.6 | 1.5% | 60 | 120 | 2 |
| 7 | 94.8 | 3.22 | TFMB | 91.55 | 10% | 60 | 120 | 2 |
| 8 | 96.37 | 3.85 | TCB | 102.6 | 10% | 60 | 120 | 2 |
| 9 | 95.73 | 3.2 | TCB | 102 | 10% | 60 | 120 | 2 |
| 10 | 96.2 | 3.1 | CB | 90.5 | 10 | 60 | 120 | 0.5 |

TFMB: trifluoromethylbenzene
TCB: trichlorobenzene

Analytical Results

Analysis by GC. The carbamoyl fluoride of the pTFMI and the pTFMI are not separated. The final product is composed very largely of pTFMI.

| | % pTcMI | % pFDCMI | % pDFCMI | % pTFMI |
|---|---|---|---|---|
| 4 | 0 | | | 72 |
| 5 | 0 | | | 73.3 |
| 6 | 2.5 | 0.8 | 2.8 | 80.7 |
| 7 | 0 | 0 | 0 | 71 |
| 8 | 0 | 0 | 0 | 73.2 |
| 9 | 0 | 0 | 0 | 73 |
| 10 | 1.5 | 0.6 | 2 | 66 |

EXAMPLES 11 TO 13

Influence of the Nature of the Catalyst and of the Final Temperature

Examples 11 to 13 are carried out according to the same procedure:

solvent/pTCMI/catalyst are introduced into the autoclave:

the mixture is heated at T1

HF is introduced over 2 h (per ⅔ g) and the pressure is adjusted to 2 bar (final 2 h at T=T1)

the mixture is brought to atmospheric pressure the mixture is heated at T2 final X hours at T=T2 the reaction mass is cooled and the residual HF is removed by sparging with nitrogen the reaction mass is diluted with methylene chloride and then quickly washed with water the analysis is carried out on the solution in methylene chloride.

| | | | | Operating conditions | | | | | |
|---|---|---|---|---|---|---|---|---|---|
| T sts | pTCMI (g) | HF equiv. (mol) | Solvent | Mass solv. (g) | Cata. | Cata. equiv. (mol) | T1 °C. | T2 °C. | X in hours |
| 11 | 96 | 3.8 | Chlorobenzene | 76.7 | SnCl$_4$ | 3.2 | 60 | 120 | 2 |
| 12 | 95.9 | 3.65 | TCB* | 102.6 | TiCl$_4$ | 3.6 | 60 | 120 | 2 |
| 13 | 95.5 | 3.7 | Chlorobenzene | 76.4 | SnCl$_4$ | 3.1 | 60 | 140 | 1 |

*TCB: 1,2,4-trichlorobenzene

Analytical Results

The yield is determined by GC analysis (the carbamoyl fluoride of the pTFMI and the pTFMI are not separated).

The pTFMI/carbamoyl fluoride of the pTFMI composition is determined by infrared analysis.

| | Yd: pTFMI + carbamoyl fluoride of the pTFMI | % pTFMI | % Carbamoyl fluoride of the PTFMI |
|---|---|---|---|
| 11 | 98.7 | 72 | 28 |
| 12 | 89.8 | 89 | 11 |
| 13 | 96.4 | 97 | 3 |

What is claimed is:

1. A process for the treatment of a mixture comprising a derivative of the formula:

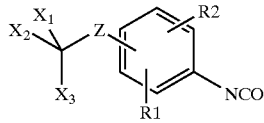

wherein:

Z represents a single bond or a chalcogen atom, wherein $X_1$, $X_2$ and $X_3$ identical or different represent halogens, with the condition that at least two halogens are other than fluorine and are exchageable by the action of liquid hydrofluoric acid;

$R_1$ and $R_2$ are halogens, alkyls, aryls or nitriles and $X_3$ is an electron-withdrawing group which does not interfere with the reaction; and a carbamoyl fluoride, wherein said derivative and said carbamoyl fluoride are subjected to a reaction temperature at least equal to 70° C. in the presence of hydrofluoric acid, and, wherein, at said temperature, the ratio of, on the one hand, the sum of the hydrofluoric acid (HF) and of the carbamoyl fluoride to, on the other hand, the sum of the exchangeable halogens, of the isocyanate functional groups and of the carbamoyl fluoride [(HF+carbamoyl fluoride)/(exchangeable halogen+isocyanate+carbamoyl fluoride)] is maintained at a value at most equal to 1.2.

2. A process according to claim 1, wherein the carbamoyl fluoride is an aromatic carbamoyl fluoride, wherein said reaction temperature is at least equal to 90° C., further in the presence of a solvent, and wherein, the ratio [(HF+carbamoyl fluoride)/(exchangeable halogen+isocyanate+carbamoyl fluoride)] is maintained at a value at most equal to 1.

3. The process as claimed in claim 1, wherein said reaction temperature is at most equal to 150° C.

4. The process as claimed in claim 2, wherein said solvent exhibits a boiling point of at least 100° C.

5. The process as claimed in claim 2, wherein the solvent is miscible with hydrofluoric acid, and is a halogenated aromatic derivative which does not react with the carbamoyl fluoride.

6. The process as claimed in claim 2, wherein said carbamoyl fluoride is added into the mixture between the solvent and the derivative or is formed in situ by addition of anhydrous hydrofluoric acid into the mixture.

7. The process as claimed in claim 1, wherein the molar ratio [(HF+carbamoyl fluoride)/(isocyanate+carbamoyl fluoride)] is at most equal to 0.8.

8. The process as claimed in claim 6, wherein the addition of the carbamoyl fluoride or of the hydrofluoric acid, in the form of a solution, takes place gradually to a heel of solvent and of said derivative brought to the reaction temperature.

9. The process as claimed in claim 8, wherein the addition is carried out at a rate such that, in the final 90% of the reaction time situated below 90° C., and the ratio [(HF+carbamoyl fluoride)/(isocyanate+carbamoyl fluoride)] is always at most equal to 0.1.

10. The process as claimed in claim 1, wherein said carbamoyl fluoride comprises an aliphatic carbon carrying at least two halogens, including at least two fluorines.

11. The process as claimed in claim 10, wherein said aliphatic carbon carrying at least two fluorines is a benzyl carbon directly attached to an aromatic ring.

12. The process as claimed in claim 11, wherein said aromatic ring is that carrying the nitrogen of the carbamoyl functional group.

13. The process as claimed in claim 1, wherein said carbamoyl fluoride corresponds to the formula:

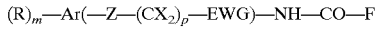

wherein:

Ar is an homocyclic aromatic ring;

the X groups, which are identical or different, represent a fluorine or a radical of formula $C_nF_{2n+1}$ with n an integer at most equal to 5;

p represents an integer at most equal to 2;

EWG represents a hydrocarbonaceous group, an electron-withdrawing group, optionally having functional groups which are inert under the conditions of the reaction, or a perfluorinated residue of formula $C_nF_{2n+1}$ with n being an integer at most equal to 8;

the total number of carbons of $—(CX_2)_p—EWG$ is between 1 and 15;

m is 0 or an integer chosen within the closed range from 1 to 4;

R is a substituent which is inert under the operating; and

Z represents a single bond or a chalcogen atom.

14. The process as claimed in claim 2, wherein the solvent is a monochlorobenzene, dichlorobenzene or trichlorobenzene.

15. The process as claimed in claim 1, wherein the mixture further comprises a catalyst whose active constituent is a Lewis acid.

16. The process as claimed in claim 15, wherein said catalyst is only added into the mixture when the latter reaches a temperature of 70° C.

17. The process as claimed in claim 15, wherein said catalyst is only added into the mixture when the substrate has, statistically, no more than a single halogen to be exchanged with the fluorine.

18. The process as claimed in claim 15, wherein said catalyst comprises an antimony(V) salt.

19. The process as claimed in claim 15, wherein said catalyst comprises a tin(IV) salt.

20. The process as claimed in claim 15, wherein said catalyst comprises a titanium(IV) salt.

21. The process as claimed in claim 15, wherein said catalyst is in the form of a halide or of a mixture of halides.

* * * * *